United States Patent
Gumbrecht et al.

(10) Patent No.: US 10,359,388 B2
(45) Date of Patent: Jul. 23, 2019

(54) ARRANGEMENT AND METHOD FOR THE ELECTROCHEMICAL ANALYSIS OF LIQUID SAMPLES BY MEANS OF LATERAL FLOW ASSAYS

(71) Applicant: SIEMENS AKTIENGESELLSCHAFT, München (DE)

(72) Inventors: Walter Gumbrecht, Herzogenaurach (DE); Peter Paulicka, Röttenbach (DE)

(73) Assignee: Siemens Aktiengesellschaft, München (DE)

( * ) Notice: Subject to any disclaimer, the term of this patent is extended or adjusted under 35 U.S.C. 154(b) by 633 days.

(21) Appl. No.: 14/377,765

(22) PCT Filed: Jan. 21, 2013

(86) PCT No.: PCT/EP2013/051026
§ 371 (c)(1),
(2) Date: Aug. 8, 2014

(87) PCT Pub. No.: WO2013/117413
PCT Pub. Date: Aug. 15, 2013

(65) Prior Publication Data
US 2015/0008144 A1 Jan. 8, 2015

(30) Foreign Application Priority Data
Feb. 8, 2012 (DE) .......... 10 2012 201 843

(51) Int. Cl.
*G01N 27/26* (2006.01)
*G01N 27/28* (2006.01)
(Continued)

(52) U.S. Cl.
CPC ......... *G01N 27/26* (2013.01); *G01N 27/30* (2013.01); *G01N 27/3272* (2013.01); *G01N 27/40* (2013.01); *G01N 33/48707* (2013.01)

(58) Field of Classification Search
CPC ....... G01N 27/26; G01N 27/28; G01N 27/30; G01N 27/327; G01N 27/3271;
(Continued)

(56) References Cited

U.S. PATENT DOCUMENTS

| 4,872,956 A | 10/1989 | Kotani et al. |
| 6,896,778 B2 | 5/2005 | Lauks |

(Continued)

FOREIGN PATENT DOCUMENTS

| DE | 19631530 A1 | 1/1998 |
| EP | 0271102 A2 | 6/1988 |

(Continued)

OTHER PUBLICATIONS

Japanese Notice of Allowance for related Japanese Application No. 2014-555989 dated May 31, 2016, with English Translation.

(Continued)

*Primary Examiner* — Susan D Leong
(74) *Attorney, Agent, or Firm* — Lempia Summerfield Katz LLC

(57) ABSTRACT

An arrangement and to a method are provided for the electrical detection of liquid samples by lateral flow assays. The lateral flow assay includes a membrane arranged on a front side of a first carrier. The first carrier is electrically insulating. On the front side of the first carrier between the carrier and the membrane, electrically conductive electrodes are arranged in direct contact with the membrane.

14 Claims, 2 Drawing Sheets

(51) Int. Cl.
*G01N 27/30* (2006.01)
*G01N 33/48* (2006.01)
*G01N 27/327* (2006.01)
*G01N 33/487* (2006.01)
*G01N 27/40* (2006.01)

(58) Field of Classification Search
CPC .. G01N 27/3272; G01N 27/40; G01N 27/403; G01N 27/413; G01N 33/48; G01N 33/48707; G01N 33/49; G01N 33/492
See application file for complete search history.

(56) References Cited

U.S. PATENT DOCUMENTS

| | | | |
|---|---|---|---|
| 8,273,227 B2* | 9/2012 | Say | A61B 5/14532 204/403.01 |
| 2002/0027072 A1 | 3/2002 | Cui et al. | |
| 2004/0043477 A1* | 3/2004 | Schibli | G01N 27/3272 435/287.1 |
| 2004/0106190 A1 | 6/2004 | Yang et al. | |
| 2004/0189311 A1* | 9/2004 | Glezer | B01J 19/0046 324/444 |
| 2008/0118398 A1 | 5/2008 | Birch et al. | |
| 2008/0199971 A1 | 8/2008 | Tondra | |
| 2009/0180927 A1 | 7/2009 | Petruno et al. | |
| 2010/0006451 A1 | 1/2010 | Gordon et al. | |
| 2012/0156709 A1* | 6/2012 | Bertin | C12Q 1/003 435/23 |
| 2014/0113384 A1* | 4/2014 | Kavusi | G01N 33/54366 436/501 |

FOREIGN PATENT DOCUMENTS

| | | |
|---|---|---|
| JP | S63148159 A | 6/1988 |
| JP | 2002090331 A | 3/2002 |
| JP | 2009210417 A | 9/2009 |
| WO | WO9803860 A1 | 1/1998 |
| WO | WO2010102279 A1 | 9/2010 |

OTHER PUBLICATIONS

German Office Action for German Application No. 10 2012 201 843.3, dated Nov. 21, 2012, with English Translation.
PCT International Search Report and Written Opinion of the International Searching Authority dated Jan. 21, 2013 for corresponding PCT/EP2013/051026.
Chinese Office Action for the related Chinese Application No. 201380009375.8, dated May 29, 2015, with English Translation.
Japanese Office action for related Japanese Application No. 2014-555989, dated Aug. 18, 2015, with English Translation.

* cited by examiner

ARRANGEMENT AND METHOD FOR THE ELECTROCHEMICAL ANALYSIS OF LIQUID SAMPLES BY MEANS OF LATERAL FLOW ASSAYS

This application is the National Stage of International Application No. PCT/EP2013/051026, filed Jan. 21, 2013, which claims the benefit of DE 10 2012 201 843.3, filed Feb. 8, 2012. The entire contents of these documents are hereby incorporated herein by reference.

BACKGROUND

The present embodiments relate to an arrangement and a method for electrical detection of liquid samples using lateral flow assays.

Lateral flow assays are in widespread use in in-vitro diagnostics (IVD). Lateral flow assays are simple in terms of handling and very cost-effective. Disadvantages of lateral flow assays include a low sensitivity, a low multiplexity and a poor quantifiability of the results.

A good quantifiability may be achieved by optical, magnetic and electrical methods, but heretofore with very low multiplexity (e.g., simultaneous measurement at a plurality of spatially separate measurement points).

U.S. Pat. No. 6,896,778 discloses an arrangement in which, for a good multiplexity, gold electrodes are arranged above cutouts of an electrically insulating carrier as an array, and the cutouts are filled with membranes composed of a polymer/microfiber matrix material. The membranes are spatially separated from one another. The membranes are ion-selective, and not suitable, for example, for immunosensors in immunoassays.

With the use of capture antibodies in immunoassays, the capture antibodies are to be immobilized directly on the gold electrodes or sensors. In an arrangement analogous to the laminated arrangement of a carrier including insulator layers and gold electrodes that is described in U.S. Pat. No. 6,896,778, where the gold electrodes are arranged above cutouts in the insulator layers in array form, a small cavity in each case arises above the gold electrodes through the surrounding insulator layer. When liquid is applied directly or via a lateral flow paper as a membrane above the arrangement, air bubbles arise in the region of the cavities and during a measurement, lead to a failure of the respective electrodes with air inclusions.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an arrangement and a method for the electrical detection of liquid samples that enable a good multiplexity in conjunction with very good sensitivity and quantifiability are provided. In this case, good multiplexity may be a multiplexity (e.g., in the range of 3- to 10-plex (sensors)). As another example, an arrangement and a method that enable a reliable measurement (e.g., without disturbing air inclusions above the electrodes) are provided.

The arrangement for the electrical detection of liquid samples by lateral flow assays includes a membrane arranged on a front side of a first carrier. The first carrier is embodied in an electrically insulating fashion, and electrically conductive electrodes are formed on the first carrier. The electrodes on the front side of the first carrier are arranged between the first carrier and the membrane, in direct contact with the membrane.

By virtue of the arrangement of the electrodes on the front side of the first carrier (e.g., on the side on which the membrane is also arranged), the electrodes may form a direct contact with the membrane. The formation of a hollow space or of a cavity, such as is present, for example, in the prior art described above, is thereby prevented. The contact area is maximized with the membrane arranged flat on the electrode, and when the liquid sample to be analyzed is applied to the membrane, the electrodes are in direct contact with the liquid sample. Air bubbles or air inclusions that may impede or completely prevent a measurement are prevented by the direct contact of electrodes and membrane, and thus also the direct contact of electrodes and the liquid sample. As a result, a reliable measurement of the sample, including in the case of multiplex measurement (e.g., with a plurality of sensors simultaneously), with very good sensitivity and quantifiability of the sample is provided.

The membrane may be configured as a closed layer via which the electrodes (e.g., all the electrodes) are connected to one another. This enables a lateral liquid transport (e.g., lateral flow) completely via the membrane (e.g., via all the electrodes).

The membrane may include or be a lateral flow paper (e.g., composed of nitrocellulose). Lateral flow paper has a high porosity and absorbs the liquid sample well and transports the liquid sample well to the electrodes. This leads there to a good wetting of the electrodes with the sample liquid to be examined. A good electrical contact via membrane saturated with liquid sample between electrodes is thus made possible. Nitrocellulose is cost-effective and, used as a membrane, has the properties described above.

The electrodes may be metal electrodes (e.g., composed of gold). Electrodes composed of metal may be relatively stable, and gold electrodes, for example, may be used well electrochemically since the gold electrodes may lead to temporally stable measurement signals and chemically are substantially inert.

The electrodes may be electrically contact-connected on the front side of the carrier (e.g., in an edge region in which the membrane is not arranged). This affords advantages, for example, if the rear side may not readily be reached for electrical contacts (e.g., as a result of encapsulation).

However, the carrier may also have in each case in the region of a respective electrode an opening passing through its thickness, from the front side to the rear side. The electrode is electrically contact-connected conductively from the front side to the rear side of the carrier. This makes it possible to prevent electrical short circuits between electrode contacts (e.g., upon contact with sample liquid on the front side of the carrier).

The carrier may include a plurality of insulating layers (e.g., layers composed of polymers and/or layers that are connected to one another by lamination). Laminated carriers composed of polymers are printed circuit boards, for example, that may be produced cost-effectively.

The membrane may be arranged in a sandwich-like fashion firstly between the front side of the first carrier in direct contact with the electrically conductive electrodes (e.g., working electrodes) of the first carrier and secondly a rear side of a second carrier in direct contact with at least one electrode (e.g., counterelectrode; exactly one electrode on the rear side of the second carrier). This arrangement enables a compact construction and short paths via the membrane between electrodes in order to establish a voltage between the working electrodes and the counterelectrode.

Each electrode on the front side of the first carrier may be in each case electrically connected to the at least one electrode on the rear side of the second carrier (e.g., via an electrical measuring instrument or measuring device for measuring current and/or voltage and/or capacitance). The electrodes may be arranged on the front side of the first carrier in a series in tandem or in array form. As a result, an electrochemical measurement is made possible, and a spatially resolved electrochemical measurement of the liquid sample in the membrane may be carried out analogously to an optical measurement in chromatography.

The method according to one or more of the present embodiments for the electrical detection of liquid samples is effected by an arrangement described above. The liquid sample is applied to the membrane and is moved by capillary forces (e.g., via the membrane to the electrodes). The membrane interconnects the electrodes (e.g., electrochemically if the membrane is filled with liquid). For example, exactly one membrane interconnects all the electrodes. As a result, a good conductivity is provided in the case of conductive liquid between the electrodes via the one membrane.

The arrangement brings about a spatial and/or temporal separation of substances in the liquid sample analogously to chromatography or with different capture molecules immobilized at different locations according to the lateral flow method. The spatial and/or temporal separation may be measured electrochemically by the electrodes in the form of current and/or voltage and/or charge changes.

In the case of the construction described, the membrane may be in direct contact with the electrodes. In each case, the contact area of each electrode with the membrane may thus be completely wetted with the liquid sample (e.g., without air inclusions above the electrode). This provides a good electrochemical measurement using the electrode, which would be prevented or at least impeded by, for example, air bubbles directly above the electrode.

The liquid sample may be a biochemical sample (e.g., a body fluid). In this regard, urine, blood, or the information thereof, for example, may be examined.

The advantages associated with the method for the electrical detection of liquid samples using the arrangement described above are analogous to the advantages described above with regard to the arrangement for the electrical detection of liquid samples using lateral flow assays.

Embodiments with advantageous developments are explained in greater detail below with reference to the figures, but without being restricted thereto.

DETAILED DESCRIPTION

Figure 1:
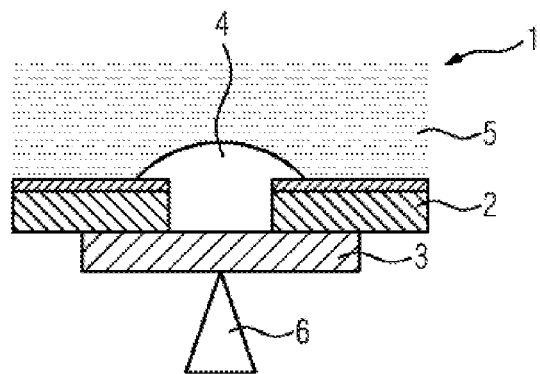
FIG. 1 illustrates a schematic sectional illustration through an arrangement for electrical detection of liquid samples according to the prior art.

An arrangement 1 for electrical detection of liquid samples 5 according to the prior art, as shown in FIG. 1, has a laminated electrode 3 of an electrode array. The arrangement 1 is shown schematically in sectional illustration. The electrode 3 is arranged below a first carrier 2, which is constructed, for example, from laminated polymer layers analogously to a printed circuit board. The electrode 3 is laminated, for example, as a gold layer onto the carrier 2. However, the electrode 3 may also be, for example, adhesively bonded or applied electrolytically.

A cutout passing through the carrier 2 is introduced in the carrier 2, above the electrode 3. The cutout may be configured, for example, in the form of a drilled hole or milled hole (e.g., in a circular fashion). Arranged in the cutout, in contact with the electrode 3, is a membrane 4 as an ion-selective layer that completely covers the free area of the electrode 3 in the cutout.

The electrode 3 is electrically contact-connected via an electrical contact 6 from the rear side (e.g., from the side of the electrode 3 that is opposite relative to the membrane 4 and is not covered by the membrane 4). A liquid sample 5 is guided via the membrane 4 and that side of the carrier 2 on which no electrodes 3 are arranged and which is opposite relative to the side with the electrodes on the carrier 2. The liquid sample is electrochemically in contact with the electrode 3 via the membrane 4. This provides that ions may move through the membrane 4 from the liquid samples 5 to the electrode 3.

A counterelectrode, not shown for the sake of simplicity, is in electrical contact with the liquid sample 5. Between the counterelectrode and the electrode 3, which functions as a working electrode, a current, voltage and/or charge change at the electrode 3 may be measured by a measuring device 10 (not shown). The measurement is carried out depending on the liquid sample 5 and serves for analyzing the sample 5. The measurement may be carried out depending on the sample flow rate and/or time and provides information about the composition or chemical/biochemical constituents of the sample 5. By way of example, blood, urine or other body fluids may serve as samples 5. However, other liquids through to gases may also be examined.

The arrangement 1 shown in FIG. 1 may be used in a sensor array or some other arrangement of sensors (e.g., in series). The electrodes 3 constitute the sensors. For a reliable measurement, it is important that no liquid 5 passes to that side of the first carrier 2 with the electrodes 3 on which the electrical contacts 6 are secured.

One disadvantage of the construction described above is the ion-selective membrane 4. The membrane 4 is not suitable for immunosensors, for example. The complicated construction is costly to produce and difficult to handle.

Figure 2:
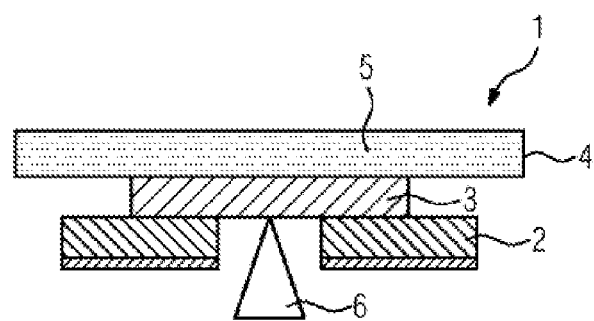
FIG. 2 illustrates a schematic sectional illustration through one embodiment of an arrangement for electrical detection of liquid samples.

FIG. 2 illustrates a schematic sectional illustration through an arrangement 1 according to one or more of the present embodiments for the electrical detection of liquid samples 5. An electrode 3 is arranged on a first, laminated carrier 2, analogously to the arrangement 1 described above under the prior art. The membrane 4 is arranged on the front side of the electrode 3, which according to one or more of the present embodiments is opposite relative to the side of the electrode 3 in contact with the carrier 2. The membrane 4 is lateral flow paper, for example, that lies flat on the electrode.

In the exemplary embodiment illustrated in FIG. 2, the electrode 3 is electrically contact-connected via an electrical contact 6 on the rear side of the electrode 3. In the laminated carrier 2, in the region of the electrode 3, on the rear side thereof, there is a cutout through which the electrical contact 6 projects as far as the electrode 3. As described below, the electrode 3 may also be contact-connected from the front side.

Figure 3:
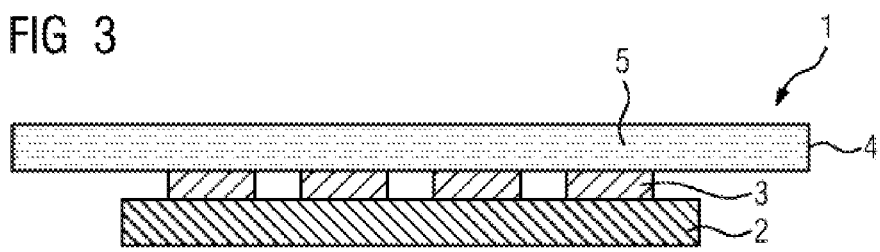
FIG. 3 illustrates a schematic sectional illustration through one embodiment of the arrangement of FIG. 2.
Figure 4:
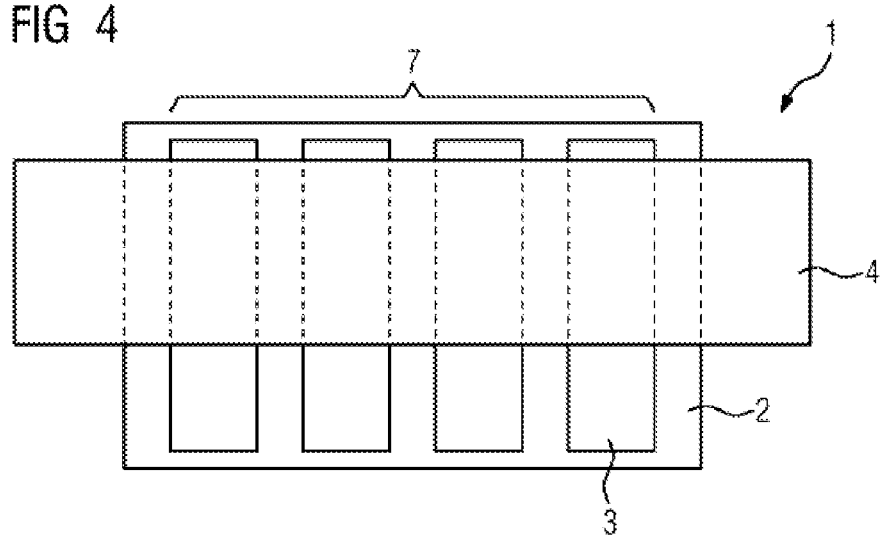
FIG. 4 illustrates a schematic illustration in a plan view of the arrangement shown in FIG. 3.

FIG. 3 and FIG. 4 show an exemplary embodiment of the arrangement 1 according to one or more of the present embodiments in which an electrical contact 6 of the electrodes 3 may be effected laterally on the front side. FIG. 3 illustrates a schematic sectional illustration through an arrangement 1 analogous to the arrangement shown in FIG. 2, but with a plurality of the electrodes 3 shown in FIG. 2 arranged in series in tandem. The electrodes 3 may also be arranged as an array (e.g., in a matrix-type fashion on the first carrier 2).

FIG. 4 illustrates a plan view of the arrangement 1 shown in FIG. 3 with electrodes 3 in a series 7. A membrane 4 (e.g., composed of lateral flow paper) is arranged in strip form on the electrodes 3 such that a lateral region of the electrodes 3 remains free for an electrical contact. In the lateral region, electrical contacts 6 may be fitted in each case to each electrode 3, this not being illustrated in the figures for the sake of simplicity.

Figure 5:
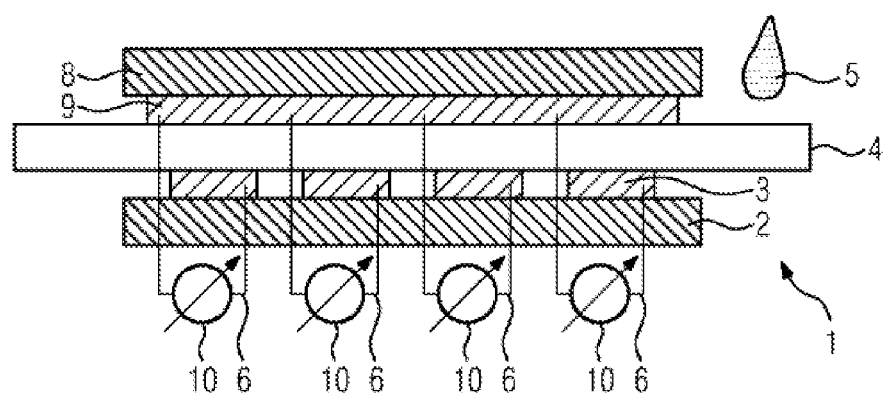
FIG. 5 illustrates a schematic sectional illustration through one embodiment of the arrangement shown in FIG. 3.

FIG. 5 shows a construction for an electrical measurement with the arrangement 1 according to one or more of the present embodiments, as shown in FIGS. 3 and 4, in a schematic sectional illustration. A second carrier 8 with an electrode 9 is arranged on the membrane 4. The membrane 4 bears in direct contact flat against the electrode 9. The electrode 9 serves as a counterelectrode. Below the membrane 4, a series of electrodes 3 serving as working electrodes is arranged in direct contact with the membrane 4. The electrodes 3 are arranged on a carrier 2, as already shown in FIGS. 2 to 4. Consequently, the membrane 4 lies in a sandwich-like fashion between the electrodes 3 on the first carrier 2 and the electrode 9 applied in a planar fashion on the second carrier 8.

As shown schematically in FIG. 5, for a measurement, the electrode 9 may be electrically connected to each electrode 3 in each case via an electrical measuring instrument or a measuring device 10. In this case, the electrodes 3, 9 may be electrically contact-connected from the side with the carrier 2, 8 through openings in the carrier 2, 8, as shown in FIG. 2, or, as described for FIG. 4, from that side of the electrodes 3, 9 that is in direct contact with the membrane 4, but in a region of the electrodes 3, 7 in which the membrane 4 is not arranged.

If a liquid sample 5 (e.g., blood or urine) is applied to the membrane 4 (e.g., lateral flow paper made of nitrocellulose in strip form or in some other form), the sample 5 is moved into and through the membrane 4 (e.g., through the porous structure of the membrane 4). The membrane 4 is thus "filled" with the sample 5. As a result of the electrical conductivity of the sample 5, the electrodes 3, 9 in direct contact with the membrane 4 are electrically or electrochemically connected to one another, and a closed electric circuit is provided in each case via the measuring device 10 between the respective electrode 3 as working electrode and the electrode 9 as counterelectrode. With electrochemical measurements, in the case of an electrode array or electrodes 3 arranged in series, the composition of the liquid sample may be examined in a spatially and temporally resolved manner. In this regard, at the individual electrodes 3 in a location-related fashion (e.g., at the location of the electrode 3), electrochemical measurements via current, voltage and/or capacitance measurements may provide information about the sample 5 situated at the location.

Analogously to chromatographic examinations, the sample composition may be analyzed, or capture molecules may be immobilized on the respective electrode 3 (e.g., different capture molecules on different electrodes 3) and enable the detection of individual substances in the sample 5. The capture molecules may also be immobilized in a spatially distributed manner in the membrane 4 in the region above the electrode 3. As a result, the arrangement 1 according to one or more of the present embodiments may be used in immunoassays.

The electrodes 3, 9 may be used, as illustrated in the figures (see FIG. 5), in a measurement set-up including working electrode 3 and counterelectrode 9. In addition, at least one reference electrode RE, not illustrated in the figures for the sake of simplicity, may also be used. Metal layers (e.g., composed of gold or platinum) may be used as electrodes or silver/silver chloride layers, or electrodes may be used, for example, as reference electrode. Other measurement set-ups that are customary in electrochemistry may also be provided.

The exemplary embodiments described above may be used in combination. The exemplary embodiments may also be combined with exemplary embodiments known from the prior art. In this regard, besides lateral flow paper (e.g., composed of nitrocellulose, membranes 4 composed of polyvinylidene fluoride, electrostatically treated nylon or polyethersulfone) may be used as membranes 4. Electrodes 3, 9 may be applied in planar fashion on the carrier 2, 8 or in a spatially structured fashion, in series in tandem, in array form in an n×m matrix including n lines and m columns, or may be provided with different height profiles.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification. Features of the independent claims may be combined with features of the dependent claims, and features of the dependent claims can be combined among one another.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An arrangement for electrical detection of liquid samples by lateral flow assays, the arrangement comprising:
   a lateral flow assay comprising:
      a first carrier configured in an electrically insulating fashion;
      a membrane;
      electrically conductive electrodes arranged on a front side of the first carrier, between the first carrier and the membrane, and in direct contact with the membrane; and
      an electrode arranged on a rear side of a second carrier, wherein the electrically conductive electrodes are arranged in a series in tandem or in array form on the front side of the first carrier, wherein the membrane is arranged in a sandwich-like fashion between the front side of the first carrier in direct contact with the electrically conductive electrodes of the first carrier and the rear side of the second carrier in direct contact with the electrode on the rear side of the second carrier, and wherein each electrode of the electrically conductive electrodes on the front side of the first carrier is electrically connected to the same electrode on the rear side of the second carrier.

2. The arrangement of claim 1, wherein the membrane is a closed layer via which the electrically conductive electrodes arranged on the front side of the first carrier are connected to one another.

3. The arrangement of claim 1, wherein the membrane comprises a lateral flow paper.

4. The arrangement of claim 1, wherein the electrically conductive electrodes on the front side of the first carrier and the electrode on the rear side of the second carrier are metal electrodes.

5. The arrangement of claim 1, wherein the electrically conductive electrodes on the front side of the first carrier are electrically contact-connected on the front side of the first carrier.

6. The arrangement of claim 1, wherein the first carrier has in each case in a region of a respective electrode of the electrically conductive electrodes on the front side of the first carrier, an opening passing through a thickness of the first carrier, from the front side to a rear side, the electrode being electrically contact-connected conductively from the front side to the rear side of the first carrier through the opening.

7. The arrangement of claim 1, wherein the first carrier comprises a plurality of insulating layers.

8. The arrangement of claim 3, wherein the membrane comprises a lateral flow paper composed of nitrocellulose.

9. The arrangement of claim 4, wherein the electrically conductive electrodes on the front side of the first carrier and the electrode on the rear side of the second carrier are metal electrodes composed of gold.

10. The arrangement of claim 5, wherein the electrically conductive electrodes on the front side of the first carrier are electrically contact-connected on the front side of the first carrier in an edge region in which the membrane is not arranged.

11. The arrangement of claim 7, wherein the insulating layers are composed of polymers, are connected to one another by lamination, or are composed of polymers and are connected to one another by lamination.

12. The arrangement of claim 1, wherein each electrode of the electrically conductive electrodes on the front side of the first carrier is electrically connected to the electrode on the rear side of the second carrier via an electrical measuring device for measuring current, voltage, capacitance, or any combination thereof.

13. The arrangement of claim 1, wherein capture molecules are immobilized on the electrically conductive electrodes on the front side of the first carrier.

14. The arrangement of claim 1, wherein the electrically conductive electrodes on the front side of the first carrier are configured to produce a spatially resolved electrochemical measurement of the liquid samples.

* * * * *